(12) United States Patent
Heske et al.

(10) Patent No.: US 9,706,980 B2
(45) Date of Patent: *Jul. 18, 2017

(54) CANNULA PROVIDED WITH A SEALING ELEMENT FOR USE IN A MEDICAL PROCEDURE

(71) Applicant: C. R. Bard, Inc., Tempe, AZ (US)

(72) Inventors: Norbert Heske, Kottgeisering (DE); Thomas Heske, Grafrath (DE)

(73) Assignee: C. R. Bard, Inc., Tempe, AZ (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/485,847

(22) Filed: Sep. 15, 2014

(65) Prior Publication Data

US 2015/0005664 A1 Jan. 1, 2015

Related U.S. Application Data

(63) Continuation of application No. 12/628,619, filed on Dec. 1, 2009, now Pat. No. 8,845,547, which is a (Continued)

(30) Foreign Application Priority Data

Mar. 29, 2003 (DE) .................................. 203 05 093

(51) Int. Cl.
*A61B 10/00* (2006.01)
*A61B 10/02* (2006.01)
(Continued)

(52) U.S. Cl.
CPC ...... *A61B 10/0233* (2013.01); *A61B 10/0275* (2013.01); *A61B 10/0283* (2013.01);
(Continued)

(58) Field of Classification Search
CPC .................... A61B 17/3498; A61B 2017/3419
(Continued)

(56) References Cited

U.S. PATENT DOCUMENTS 3,004,536 A 10/1961 Walter
3,565,074 A 2/1971 Foti et al.
(Continued)

FOREIGN PATENT DOCUMENTS

DE 4041614 C1 10/1992
DE 10034297 A1 4/2001
(Continued)

*Primary Examiner* — Michael C Stout

(57) ABSTRACT

A cannula arrangement includes an outer tube and an inner tube. The outer tube has a proximal end and a distal end. The inner tube is disposed within the outer tube to define a space between an inner surface of the outer tube and an outer surface of the inner tube. A flexible sealing element is sized to seal the space between the inner surface of the outer tube and the outer surface of the inner tube. The flexible sealing element is connected to a proximal portion of the outer tube. The flexible sealing element has a cantilevered portion that longitudinally extends proximally from the proximal end of the outer tube. The cantilevered portion has an inner surface portion that does not contact the inner tube, and a proximal portion configured to define an interior edge to contact the outer surface of the inner tube.

3 Claims, 4 Drawing Sheets

Related U.S. Application Data continuation of application No. 10/549,820, filed as application No. PCT/EP2004/003327 on Mar. 29, 2004, now Pat. No. 7,645,239.

(51) Int. Cl.
*A61B 17/34* (2006.01)
*G01N 1/08* (2006.01)

(52) U.S. Cl.
CPC ...... *A61B 17/3417* (2013.01); *A61B 17/3421* (2013.01); *A61B 17/3462* (2013.01); *A61B 17/3498* (2013.01); *G01N 1/08* (2013.01); *A61B 17/3474* (2013.01)

(58) Field of Classification Search
USPC ............... 600/547, 567; 604/167.01, 167.02, 604/167.03, 167.04
See application file for complete search history.

(56) References Cited

U.S. PATENT DOCUMENTS

| | | | |
|---|---|---|---|
| 3,606,878 A | 9/1971 | Kellogg, Jr. | |
| 3,844,272 A | 10/1974 | Banko | |
| 3,994,287 A | 11/1976 | Turp et al. | |
| 4,490,137 A | 12/1984 | Moukheibir | |
| 4,649,904 A | 3/1987 | Krauter et al. | |
| RE33,258 E | 7/1990 | Onik et al. | |
| 4,940,061 A | 7/1990 | Terwilliger | |
| 4,958,625 A | 9/1990 | Bates et al. | |
| 5,025,797 A | 6/1991 | Baran | |
| 5,125,413 A | 6/1992 | Baran | |
| 5,282,476 A | 2/1994 | Terwilliger | |
| 5,335,671 A | 8/1994 | Clement | |
| 5,368,045 A | 11/1994 | Clement et al. | |
| 5,368,574 A * | 11/1994 | Antonacci | A61M 25/0662 604/167.02 |
| 5,400,798 A | 3/1995 | Baran | |
| 5,526,822 A | 6/1996 | Burbank et al. | |
| 5,546,957 A | 8/1996 | Heske | |
| 5,549,576 A | 8/1996 | Patterson et al. | |
| 5,584,850 A * | 12/1996 | Hart | A61B 17/3498 604/278 |
| 5,601,585 A | 2/1997 | Banik et al. | |
| 5,617,874 A | 4/1997 | Baran | |
| 5,649,547 A | 7/1997 | Ritchart et al. | |
| 5,655,542 A | 8/1997 | Weilandt | |
| 5,657,963 A | 8/1997 | Hinchliffe et al. | |
| 5,693,031 A | 12/1997 | Ryan et al. | |
| 5,709,697 A | 1/1998 | Ratcliff et al. | |
| 5,718,237 A * | 2/1998 | Haaga | A61B 10/0275 128/DIG. 8 |
| 5,752,923 A | 5/1998 | Terwilliger | |
| 5,752,938 A * | 5/1998 | Flatland | A61B 17/3462 604/167.01 |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,788,651 A | 8/1998 | Weilandt | |
| 5,807,282 A | 9/1998 | Fowler | |
| 5,817,034 A | 10/1998 | Milliman et al. | |
| 5,823,970 A | 10/1998 | Terwilliger | |
| 5,830,219 A | 11/1998 | Bird et al. | |
| D403,405 S | 12/1998 | Terwilliger | |
| 5,857,982 A | 1/1999 | Milliman et al. | |
| 5,865,807 A | 2/1999 | Blake, III | |
| 5,910,121 A | 6/1999 | Paolo et al. | |
| 5,913,857 A | 6/1999 | Ritchart et al. | |
| 5,928,164 A | 7/1999 | Burbank et al. | |
| 5,944,673 A | 8/1999 | Gregoire et al. | |
| 5,951,490 A | 9/1999 | Fowler | |
| 5,964,716 A | 10/1999 | Gregoire et al. | |
| 5,971,939 A | 10/1999 | Cooper et al. | |
| 5,976,164 A | 11/1999 | Mueller et al. | |
| 5,980,469 A | 11/1999 | Burbank et al. | |
| 5,980,493 A | 11/1999 | Smith et al. | |
| 6,007,495 A | 12/1999 | Matula | |
| 6,007,496 A | 12/1999 | Brannon | |
| 6,007,497 A | 12/1999 | Huitema | |
| 6,019,733 A | 2/2000 | Farascioni | |
| 6,022,324 A | 2/2000 | Skinner | |
| 6,027,458 A | 2/2000 | Janssens | |
| 6,033,369 A * | 3/2000 | Goldenberg | A61B 10/025 600/567 |
| 6,036,657 A | 3/2000 | Milliman et al. | |
| 6,050,955 A | 4/2000 | Bryan et al. | |
| 6,063,037 A | 5/2000 | Mittermeier et al. | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,126,617 A | 10/2000 | Weilandt et al. | |
| 6,142,955 A | 11/2000 | Farascioni et al. | |
| 6,142,980 A * | 11/2000 | Schalk | A61M 1/0031 137/512.3 |
| 6,162,187 A | 12/2000 | Buzzard et al. | |
| 6,162,203 A * | 12/2000 | Haaga | A61B 10/0275 128/898 |
| 6,165,136 A | 12/2000 | Nishtala | |
| 6,193,673 B1 | 2/2001 | Viola et al. | |
| 6,196,978 B1 | 3/2001 | Weilandt et al. | |
| 6,200,262 B1 * | 3/2001 | Ouchi | A61B 1/00137 600/154 |
| 6,213,957 B1 | 4/2001 | Milliman et al. | |
| 6,221,029 B1 * | 4/2001 | Mathis | A61B 10/0233 600/564 |
| 6,221,050 B1 | 4/2001 | Ishida | |
| 6,228,068 B1 | 5/2001 | Yoon | |
| 6,231,522 B1 | 5/2001 | Voegele et al. | |
| 6,241,687 B1 | 6/2001 | Voegele et al. | |
| 6,273,861 B1 * | 8/2001 | Bates | A61B 10/0275 600/567 |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,290,476 B1 * | 9/2001 | Wu | F04B 33/005 417/549 |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,402,701 B1 | 6/2002 | Kaplan et al. | |
| 6,409,967 B1 * | 6/2002 | McIntosh | A61M 1/3627 137/238 |
| 6,419,278 B1 * | 7/2002 | Cunningham | F16L 33/2071 285/256 |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdorff et al. | |
| 6,436,054 B1 | 8/2002 | Viola et al. | |
| 6,436,108 B1 * | 8/2002 | Mears | A61B 17/12013 606/139 |
| 6,439,541 B1 * | 8/2002 | Nosel | 606/139 |
| 6,488,636 B2 | 12/2002 | Bryan et al. | |
| 6,506,181 B2 | 1/2003 | Meng et al. | |
| 6,514,215 B1 * | 2/2003 | Ouchi | A61B 17/3498 251/149.1 |
| 6,540,694 B1 | 4/2003 | Van Bladel et al. | |
| 6,540,761 B2 | 4/2003 | Houser | |
| 6,551,255 B2 | 4/2003 | Van Bladel et al. | |
| 6,554,779 B2 | 4/2003 | Viola et al. | |
| 6,585,664 B2 | 7/2003 | Burdorff et al. | |
| 6,638,235 B2 | 10/2003 | Miller et al. | |
| 6,659,105 B2 | 12/2003 | Burbank et al. | |
| 6,730,043 B2 | 5/2004 | Krueger et al. | |
| 6,752,768 B2 | 6/2004 | Burdorff et al. | |
| 6,758,824 B1 | 7/2004 | Miller et al. | |
| 6,764,495 B2 | 7/2004 | Lee et al. | |

(56) References Cited

U.S. PATENT DOCUMENTS

| | | |
|---|---|---|
| 6,849,080 B2 | 2/2005 | Lee et al. |
| 7,037,303 B2 | 5/2006 | Beaufore et al. |
| 7,083,626 B2 | 8/2006 | Hart et al. |
| 7,153,274 B2 | 12/2006 | Stephens et al. |
| 7,156,836 B2 | 1/2007 | Teo et al. |
| 7,189,206 B2 | 3/2007 | Quick et al. |
| 7,226,424 B2 | 6/2007 | Ritchart et al. |
| 7,241,276 B2 | 7/2007 | Argentine et al. |
| 7,347,829 B2 | 3/2008 | Mark et al. |
| 7,645,239 B2 | 1/2010 | Heske et al. |
| 7,648,466 B2 | 1/2010 | Stephens et al. |
| 7,740,598 B2 | 6/2010 | Heske et al. |
| 7,789,861 B2 | 9/2010 | Franer |
| 7,901,379 B2 | 3/2011 | Argentine et al. |
| RE42,379 E * | 5/2011 | Loomas .............. A61B 17/3462 277/505 |
| 8,231,525 B2 * | 7/2012 | Cohen ................ A61B 1/00137 600/154 |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0047183 A1 | 11/2001 | Privitera et al. |
| 2002/0016555 A1 | 2/2002 | Ritchart et al. |
| 2002/0045840 A1 | 4/2002 | Voegele et al. |
| 2002/0045842 A1 | 4/2002 | Van Bladel et al. |
| 2002/0068878 A1 | 6/2002 | Jasonni et al. |
| 2002/0082519 A1 | 6/2002 | Miller et al. |
| 2002/0110484 A1 | 8/2002 | McIntosh |
| 2002/0111585 A1 | 8/2002 | Lafontaine |
| 2002/0120212 A1 | 8/2002 | Ritchart et al. |
| 2002/0151822 A1 | 10/2002 | Burdorff et al. |
| 2002/0156395 A1 | 10/2002 | Stephens et al. |
| 2002/0165492 A1 | 11/2002 | Davey et al. |
| 2003/0009079 A1 | 1/2003 | Beaufore et al. |
| 2003/0088153 A1 * | 5/2003 | Carrillo, Jr. ....... A61M 25/0606 604/506 |
| 2003/0093058 A1 * | 5/2003 | Siang Teo .............. A61B 1/015 600/564 |
| 2003/0199753 A1 * | 10/2003 | Hibner .............. A61M 25/0075 600/114 |
| 2004/0002632 A1 * | 1/2004 | D'Arrigo ........... A61B 10/0283 600/411 |
| 2004/0010230 A1 * | 1/2004 | Dittrich .............. A61B 17/0206 600/210 |
| 2004/0059297 A1 | 3/2004 | Racenet et al. |
| 2004/0060563 A1 * | 4/2004 | Rapacki ............ A61B 17/3462 604/167.06 |
| 2004/0186393 A1 | 9/2004 | Leigh et al. |
| 2004/0215103 A1 | 10/2004 | Mueller, Jr. et al. |
| 2004/0249278 A1 | 12/2004 | Krause |
| 2004/0249307 A1 | 12/2004 | Thompson et al. |
| 2005/0004492 A1 | 1/2005 | Burbank et al. |
| 2005/0010131 A1 | 1/2005 | Burbank et al. |
| 2005/0027210 A1 | 2/2005 | Miller |
| 2005/0043682 A1 * | 2/2005 | Kucklick .......... A61B 17/12022 128/207.14 |
| 2005/0059934 A1 | 3/2005 | Wenchell et al. |
| 2005/0096605 A1 * | 5/2005 | Green ................ A61B 17/3498 604/167.03 |
| 2005/0113757 A1 * | 5/2005 | McFarlane ......... A61B 17/3421 604/164.09 |
| 2005/0131349 A1 * | 6/2005 | Albrecht .............. A61M 39/06 604/246 |
| 2005/0165328 A1 | 7/2005 | Heske et al. |
| 2005/0165356 A1 * | 7/2005 | Pasqualucci ....... A61B 17/3462 604/167.06 |
| 2005/0203439 A1 | 9/2005 | Heske et al. |
| 2005/0212221 A1 | 9/2005 | Smith et al. |
| 2006/0041232 A1 | 2/2006 | Stearns et al. |
| 2006/0047293 A1 | 3/2006 | Haberland et al. |
| 2006/0129062 A1 | 6/2006 | Nicoson et al. |
| 2006/0129064 A1 | 6/2006 | Conway et al. |
| 2007/0032741 A1 | 2/2007 | Hibner et al. |
| 2007/0149894 A1 | 6/2007 | Heske et al. |
| 2008/0154151 A1 | 6/2008 | Ritchart et al. |
| 2008/0319396 A1 | 12/2008 | Smith |

FOREIGN PATENT DOCUMENTS

| | | |
|---|---|---|
| DE | 10026303 A1 | 2/2002 |
| DE | 20204363 U1 | 5/2002 |
| DE | 20204362 U1 | 7/2002 |
| DE | 20209525 U1 | 11/2002 |
| EP | 0433717 A1 | 6/1991 |
| EP | 0890339 A1 | 1/1999 |
| EP | 0995400 A1 | 4/2000 |
| EP | 1074271 A2 | 2/2001 |
| GB | 2018601 A | 10/1979 |
| WO | 9628097 A1 | 9/1996 |
| WO | 9825522 A1 | 6/1998 |
| WO | 0030546 A1 | 6/2000 |
| WO | 0059378 A2 | 10/2000 |
| WO | 0232318 A1 | 4/2002 |
| WO | 02069808 A2 | 9/2002 |

* cited by examiner

CANNULA PROVIDED WITH A SEALING ELEMENT FOR USE IN A MEDICAL PROCEDURE

CROSS REFERENCE TO RELATED APPLICATIONS

This is a continuation of U.S. patent application Ser. No. 12/628,619, filed Dec. 1, 2009, now U.S. Pat. No. 8,845,547, which is a continuation of U.S. patent application Ser. No. 10/549,820, filed Sep. 20, 2005, now U.S. Pat. No. 7,645, 239, as a national application under 35 U.S.C. §371 of International Application Serial No. PCT/EP04/03327 filed Mar. 29, 2004, which claims priority to DE 20305093.2, filed Mar. 29, 2003, the entireties of which are incorporated herein by reference.

This application is related to U.S. patent application Ser. No. 11/680,917, filed Mar. 1, 2007, now U.S. Pat. No. 7,740,598, which is a continuation of U.S. patent application Ser. No. 10/549,820, filed Sep. 20, 2005, now U.S. Pat. No. 7,645,239.

MICROFICHE APPENDIX

None

GOVERNMENT RIGHTS IN PATENT

None

BACKGROUND OF THE INVENTION

1. Field of the Invention

The present invention relates to medical devices, and, more particularly, to a cannula provided with a sealing element for use in a medical procedure.

2. Description of the Related Art

Known from DE GMS 202 09 525.8 is a coaxial cannula that can be inserted into tissue and in which a biopsy needle unit can be employed. A seal is provided between the interior wall of the coaxial cannula and the exterior wall of the biopsy needle unit in order to, first, prevent fluid from escaping and, second, to make it possible to create a vacuum in the tissue to be biopsied. DE GMS 202 09 525.8 states that the sealing function of the seal must be created such that it prevents air from entering or escaping and also prevents fluid from escaping.

Such a seal has led to problems in practice. When inserting the biopsy needle unit into the coaxial cannula and during subsequent positioning of the needle unit, the air that has penetrated into the coaxial cannula as a result of the insertion process is sealed in and air bubbles form that cause problems with the ultrasound or MR images made while the needle is being positioned so that precise positioning is not possible due to the air occlusions.

SUMMARY OF THE INVENTION

The invention relates to a coaxial cannula that can be employed in tissue, in which for removing tissue are a biopsy needle unit with specimen removal space and a longitudinally movable specimen separating device that coaxially encloses the biopsy needle on the exterior wall, and whereby the coaxial cannula has on its proximal end a sealing element that encloses the space between the interior wall of the coaxial cannula and the exterior wall of the specimen separating device.

The sealing element releases the air outlet when the needle unit is inserted and prevents air from entering after the needle unit has been positioned and a vacuum has been created in the biopsy needle interior space.

Due to such an embodiment of the seal, on the one hand air that has been compressed by inserting the needle unit can escape so that no occluded air bubbles are formed and ultrasound or MR images are not affected or disrupted.

The invention in one form thereof is directed to a cannula arrangement. The cannula arrangement includes an outer tube and an inner tube. The outer tube has a proximal end and a distal end. The inner tube is disposed within the outer tube to define a space between an inner surface of the outer tube and an outer surface of the inner tube. A sealing element is mounted at the proximal end of the outer tube. The sealing element has a projecting portion that projects proximally from the proximal end of the outer tube. The projecting portion has a projecting end that has an interior edge to contact the outer surface of the inner tube.

The invention in another form thereof is directed to a cannula. The cannula includes a tube having a proximal end and a distal end. A sealing element is mounted at the proximal end of the tube. The sealing element has a projecting portion that projects proximally from the proximal end of the tube. The projecting portion has a projecting end that is curved inwardly and has an interior sealing edge.

The invention in another form thereof is directed to a method of venting a cannula. The method includes forming a seal with a sealing element projecting from a proximal end of an outer tube so that an edge of the sealing element is flexibly pressing against an outer surface of an inner tube slidably disposed within the outer tube to form the seal, the seal resisting a distal movement of a fluid into a space defined by an inner surface of the outer tube and the outer surface of the inner tube; and moving the edge at least in part away from the outer surface of the inner tube to break the seal and allow the passage of a proximally-moving fluid from the space.

The invention in another form thereof is directed to a medical device. The medical device includes a coaxial cannula for use in tissue, the coaxial cannula having an interior wall. A biopsy needle unit is configured for insertion into the coaxial cannula. The biopsy needle unit has an exterior surface, and when inserted into the coaxial cannula an intermediate space is formed between the interior wall of the coaxial cannula and the exterior surface of the biopsy needle unit. An elastic sealing element defines a sealing lip, the sealing lip having an interior edge. The elastic sealing element is mounted to the coaxial cannula, wherein the interior edge of the sealing lip is located to seal against the exterior surface of the biopsy needle unit.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings.

Exemplary embodiments are described in detail as follows.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
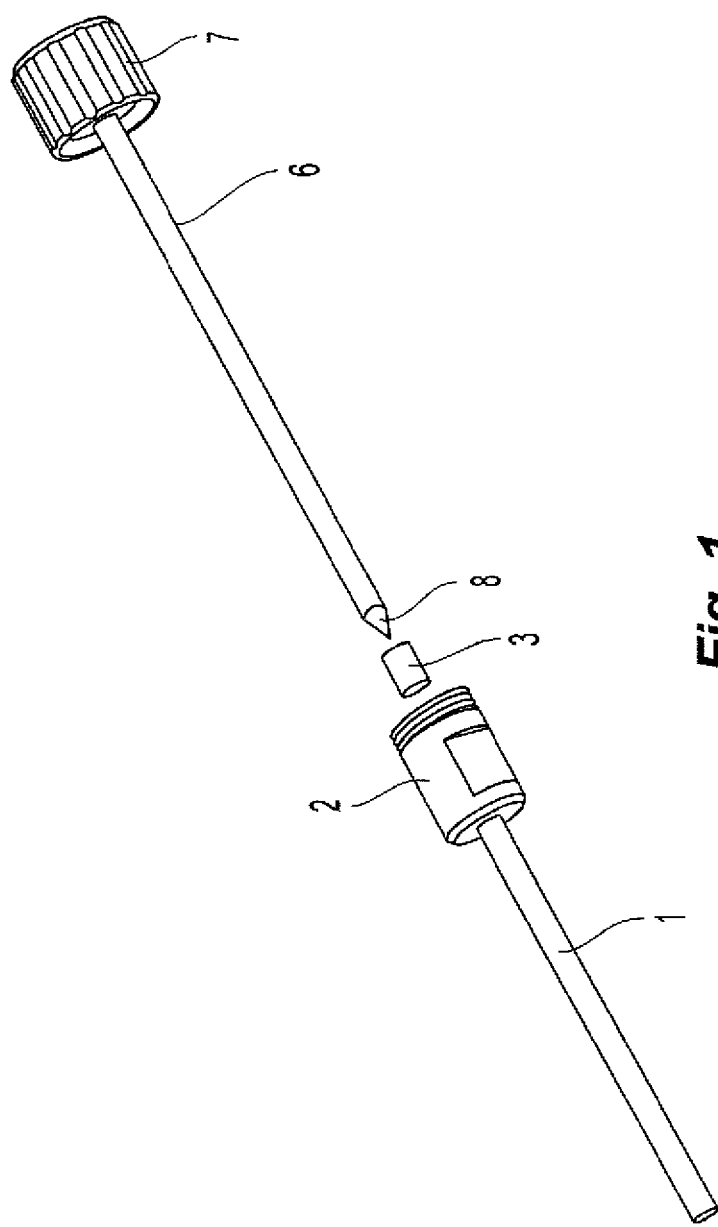
FIG. 1 is an exploded depiction of a coaxial cannula with mandrel.
Figure 2:
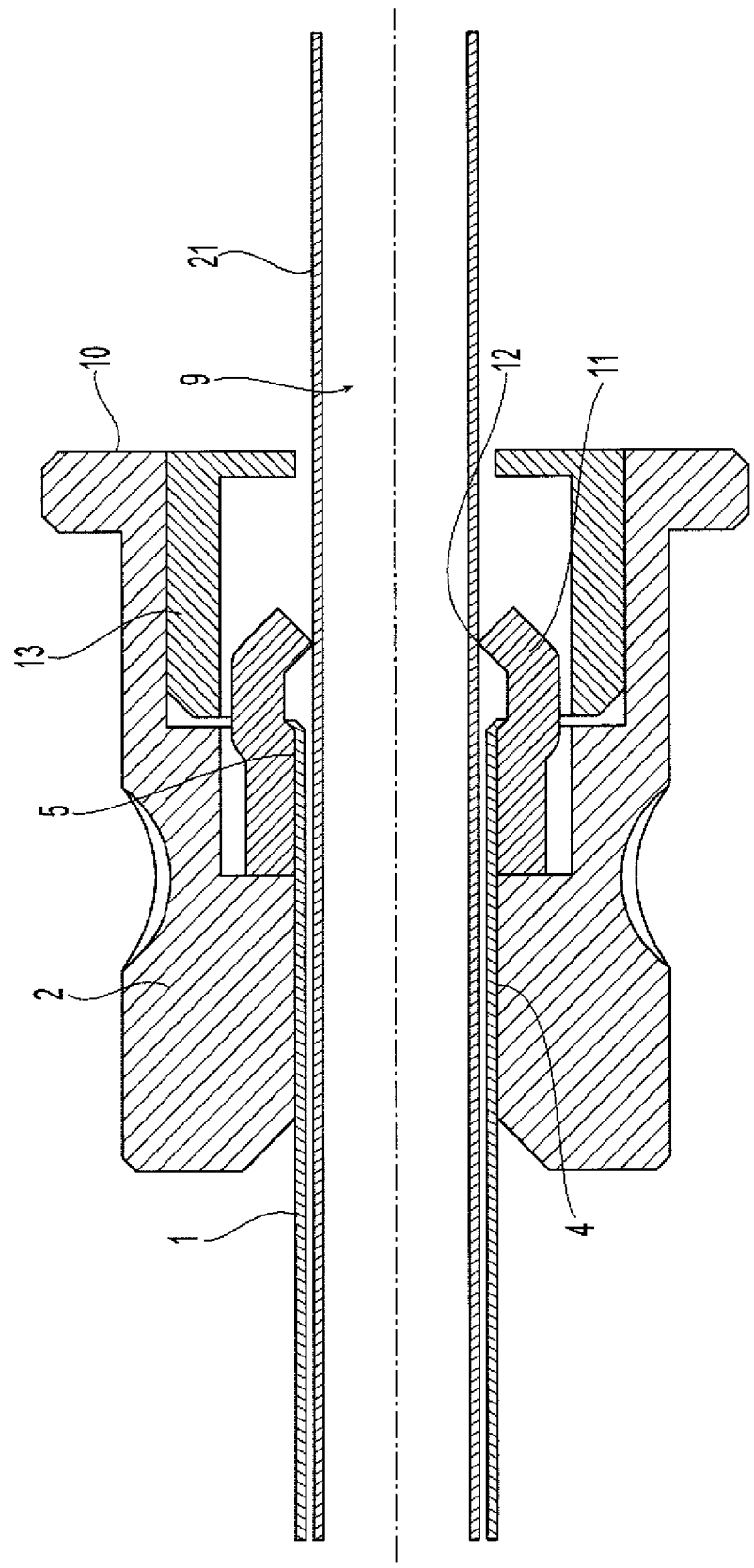
FIG. 2 is a section through the cap of a coaxial cannula (variant A, enlarged)

Referring now to the drawings, and more particularly to FIGS. 1 and 2, there is shown a coaxial cannula arrangement in accordance with an embodiment of the invention.

FIG. 1 illustrates a coaxial cannula with mandrel in an exploded drawing. A cap 2 is connected to the coaxial cannula tube 1 ("tube" for short). For attaching the tube 1, the latter projects into an interior bore 4 of the cap 2 at its proximal end 5 into the cap (FIG. 2). For example, a clamping seat holds the proximal tube end 5 in the cap. A sealing element 3, e.g., a hose piece, is placed over the proximal tube end 5. For inserting the coaxial cannula into the tissue, a mandrel 6 (press-in mandrel) is inserted into the coaxial cannula and the mandrel cap 7 is screwed to the cap 2. When assembled, the mandrel tip 8 projects beyond the distal end of the tube.

The coaxial cannula is inserted together with the mandrel into the tissue, e.g., by pressing it in, specifically such that, for example by means of ultrasound equipment, the mandrel tip of the mandrel is guided to or placed in the vicinity of the tissue to be examined.

Once the coaxial cannula has been inserted by means of the mandrel, the mandrel is withdrawn and removed; e.g., by unscrewing the connection to the proximal end. In order to prevent rotation or a change in the positioned coaxial cannula, surfaces are provided on the coaxial cannula in which a fork or clamp that is connected via additional elements engages, e.g., to the operating or examining table, so that the coaxial cannula is held in the selected position.

After the coaxial cannula has been inserted and positioned, and after the mandrel has been removed, the needle unit 9 of a vacuum biopsy device with or without an externally arranged cutting sleeve 21 (specimen separating device) is inserted into the tube 1 of the coaxial cannula (FIG. 2). The needle unit 9 comprises, for example, a hollow needle with a cutting sleeve 21 that encloses it coaxially and has a cutting edge on the distal side. However, the needle apparatus can also be an exterior hollow needle in the hollow space of which the cutting device is coaxially arranged. Instead of the mandrel cap, now the end face, for example of a sterile guide roller 13 of the vacuum biopsy equipment, sits against the proximal end face 10 of the cap 2 (see also FIGS. 3 and 4). After insertion, the end face of the guide roller 13 of the vacuum biopsy device sits on the end face 10 of the cap. When the needle unit is inserted, the air that penetrated after the removal of the mandrel can at first escape until the sealing lip 11 is drawn to the exterior surface of the needle unit by a vacuum created in the hollow needle; i.e., the part of the sealing element that projects beyond the cannula tube on the proximal side is designed so that when the needle unit is inserted a slight gap remains open between the sealing lip and the exterior surface of the needle unit; this occurs, for instance, by having only one edge 12 of the sealing lip touch the exterior surface. When a vacuum is created in the hollow space of the biopsy needle, the underpressure increases the pressure force so that the sealing lip 11, that is, the free hose end, is pressed against the exterior surface of the needle unit, thus preventing the entry of more air.

The use of an appropriately dimensioned hose that is placed over the proximal end of the coaxial hose is a simple, inexpensive, yet effective embodiment of the sealing element. Care should be taken that the flexibility of the hose is such that during insertion the suction effect at slight underpressure securely closes the gap present between the interior wall of the coaxial cannula and the exterior wall of the needle unit. Specifically, this is attained by using suction to draw the proximal end, e.g., the interior edge, of the hose against the exterior side of the needle unit. For this reason the proximal end of the hose is preferably slightly curved toward the needle unit so that when the vacuum is created the projecting part of the hose piece is drawn inward and pressed against the exterior surface of the needle unit. Removing the vacuum, the underpressure, in the needle hollow space cancels the sealing effect and the gap reopens due to the elasticity of the hose.

However, the sealing element can also be part of the vacuum biopsy device (e.g., in accordance with DE GMS 202 04 363), in particular when the biopsy device is equipped with a guide roller. In this case a stopper on the distal side at the guide roller is provided that acts as a sealer to engage a corresponding coupling bore in the cap of the coaxial cannula. If the sealing elements do not enter into the counterpart until just prior to the device being placed onto the counterpart into the countercoupling parts, the air can exit first. Thus, the effect does not occur until just before the closing so that no air bubbles or air occlusions disrupt the ultrasound or MR images.

If an intermediate piece is used between the guide roller and the proximal surface of the coaxial cap to reduce the penetration depth of the biopsy needle unit, the intermediate piece has one coupling piece on the distal side and one on the proximal side so that the stopper of the guide roller can, first, act as a seal, and second, the intermediate piece can act as a seal in the coupling cap. The intermediate space between the needle unit and the coaxial cannula is not closed until just prior to the final positioning of the needle unit so that the air can escape and is not compressed.

Figure 3:
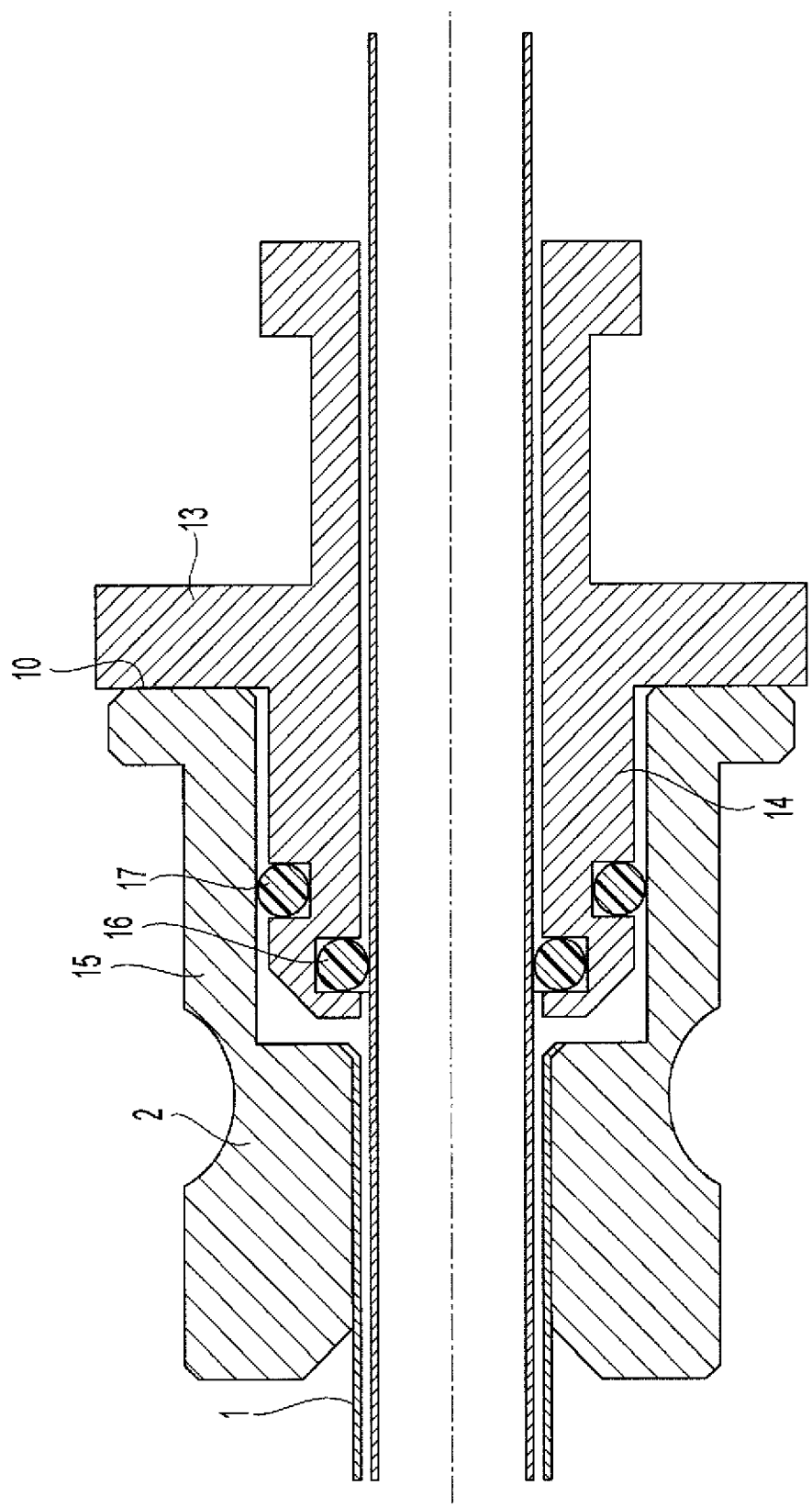
FIG. 3 is a section through the cap of a coaxial cannula acting together with a guide roller on the biopsy device (variant B, enlarged)
Figure 4:
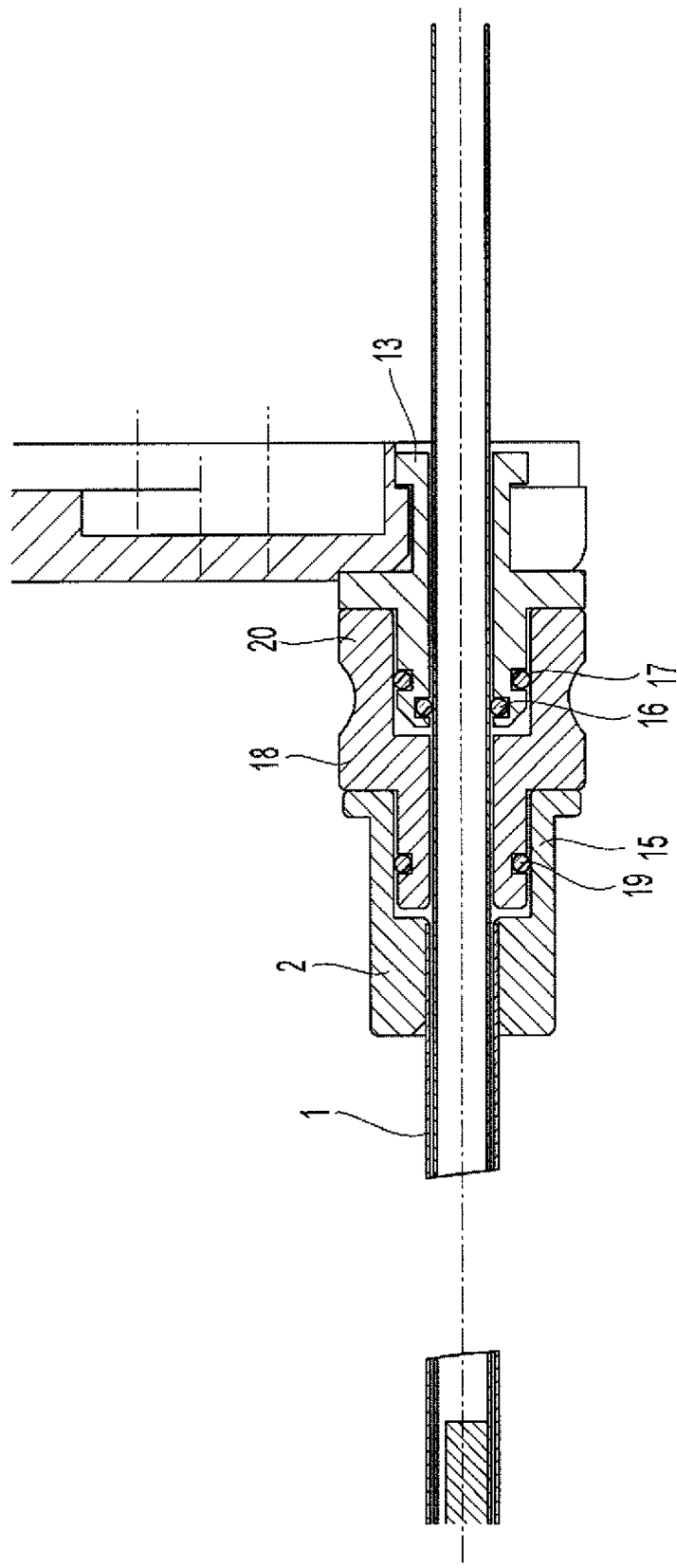
FIG. 4 is a section through the coaxial cannula cap using an intermediate piece and a guide roller on the vacuum biopsy device.

In the examples illustrated in FIGS. 3 and 4, alternatives for the embodiment of the sealing function, the guide roller 13 does not sit flush with the end face 10 of the cap, and there is also no sealing element arranged on the proximal end of the tube 1, but instead the guide roller of the biopsy device has a stopper 14 that is inserted into a coupling counterpart 15 provided in the cap 2. The stopper seals the exterior surface of the needle unit against the guide roller via the seal 16. The cap is sealed against the stopper of the guide roller by means of the seal 17. Both seals are designed, for example, as O-rings. Because the stopper is kept very short in its longitudinal extension (e.g. stopper length is 5 mm), the sealing effect does not occur until just prior to placing the guide roller on the cap. In other words, the sealing effect does not occur until just before the needle tip is positioned. Air that is present in the coaxial cannula can escape until the sealing effect occurs.

FIG. 4 illustrates the same arrangement as FIG. 3, but in this case in order to reduce the penetration depth of the needle unit an intermediate piece 18 is inserted between cap 2 and guide roller 13. The intermediate piece has on its distal side a stopper 14 that is inserted into the coupling counterpiece. The seal between the cap-side coupling counterpiece of the coaxial cannula and the stopper 14 occurs via the seal 19. The stopper 14 of the guide roller is the same as that already described (FIG. 3) and is inserted into a coupling counterpiece 20 of the intermediate piece 18, which is arranged on the proximal side. The sealing arrangement is the same as that described for FIG. 3. In this case, as well, the sealing effect does not occur until just before the tip of the needle unit is brought into its final position. This means that the air that has penetrated can escape from the hollow cannula during the insertion process. The intent of both solutions is that the air that has penetrated into the coaxial cannula when the mandrel is exchanged for the needle unit can escape to the greatest extent possible when the needle unit is inserted so that no disruptions occur during the use of ultrasound or MR.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A cannula assembly, comprising:
   a tube having a proximal end, a proximal portion, and a distal portion;
   a flexible sealing element connected to the proximal portion of the tube, the flexible sealing element having a longitudinal axis coaxial with the tube, the flexible sealing element having a cantilevered portion that longitudinally extends a longitudinal distance parallel to the longitudinal axis in a proximal direction from the proximal end of the outer tube, the cantilevered portion having an exposed inner surface portion that longitudinally extends from the proximal end of the tube, the cantilevered portion having a wall portion proximal the exposed inner surface portion, the wall portion configured to define an interior sealing edge;
   a cap connected to the tube, the flexible sealing element being disposed within the cap; and
   a guide roller of a vacuum biopsy device annularly interposed between the cap and the sealing edge of the wall portion of the flexible sealing element.

2. A cannula assembly, comprising:
   a tube having a proximal end, a proximal portion, and a distal portion;
   a flexible sealing element connected to the proximal portion of the tube, the flexible sealing element having a longitudinal axis coaxial with the tube, the flexible sealing element having a cantilevered portion that longitudinally extends a longitudinal distance parallel to the longitudinal axis in a proximal direction from the proximal end of the outer tube, the cantilevered portion having an exposed inner surface portion that longitudinally extends from the proximal end of the tube, the cantilevered portion having a wall portion proximal the exposed inner surface portion, the wall portion configured to define an interior sealing edge;
   a cap connected to the tube, the flexible sealing element being disposed within the cap; and
   a guide roller of a vacuum biopsy device annularly interposed between the cap and the cantilevered portion of the flexible sealing element.

3. A cannula assembly, comprising:
   a tube having a proximal end, a proximal portion, and a distal portion;
   a flexible sealing element connected to the proximal portion of the tube, the flexible sealing element having a longitudinal axis coaxial with the tube, the flexible sealing element having a cantilevered portion that longitudinally extends a longitudinal distance parallel to the longitudinal axis in a proximal direction from the proximal end of the outer tube, the cantilevered portion having an exposed inner surface portion that longitudinally extends from the proximal end of the tube, the cantilevered portion having a wall portion proximal the exposed inner surface portion, the wall portion configured to define an interior sealing edge; and
   a cap connected to the tube, the flexible sealing element being disposed within the cap, the cap configured to receive a guide roller of a vacuum biopsy device at a location annularly interposed between the cap and the cantilevered portion of the flexible sealing element.

* * * * *